US008409573B2

(12) United States Patent
Boumsell et al.

(10) Patent No.: US 8,409,573 B2
(45) Date of Patent: Apr. 2, 2013

(54) ANTI-CD71 MONOCLONAL ANTIBODIES AND USES THEREOF FOR TREATING MALIGNANT TUMOR CELLS

(75) Inventors: Laurence Boumsell, Paris (FR); Jean Kadouche, Paris (FR); Armand Bensussan, Paris (FR)

(73) Assignees: Mablife, Evry (FR); Institut National de la Sante et de la Recherche Medicale (INSERM), Paris (FR)

( * ) Notice: Subject to any disclaimer, the term of this patent is extended or adjusted under 35 U.S.C. 154(b) by 1101 days.

(21) Appl. No.: 11/922,025

(22) PCT Filed: Jun. 14, 2006

(86) PCT No.: PCT/IB2006/002331
§ 371 (c)(1),
(2), (4) Date: Sep. 29, 2008

(87) PCT Pub. No.: WO2007/000671
PCT Pub. Date: Jan. 4, 2007

(65) Prior Publication Data
US 2011/0311544 A1    Dec. 22, 2011

Related U.S. Application Data

(63) Continuation of application No. 11/154,262, filed on Jun. 15, 2005, now Pat. No. 7,736,647.

(51) Int. Cl.
*A61K 39/00* (2006.01)
(52) U.S. Cl. ............... 424/133.1; 424/138.1; 424/139.1; 424/141.1; 424/143.1
(58) Field of Classification Search .................. None
See application file for complete search history.

(56) References Cited

U.S. PATENT DOCUMENTS
5,756,097 A    5/1998   Landucci et al.

FOREIGN PATENT DOCUMENTS
WO    WO-91/14452 A1    10/1991
WO    WO-2005/121179 A2    12/2005

OTHER PUBLICATIONS

Jain. Barriers to drug delivery in solid tumors. Scientific American, 1994. pages 58-64.*
Chatterjee, Foon, and Kohler. Idiotypic antibody immunotherapy of cancer. Cancer Immunology and Immunotherapy, 1994. vol. 38, pp. 75-82.*
Dermer. Another anniversary for the war on cancer. Biotechnology, 1994. vol. 12, p. 320.*
Gura. Systems for identifying new drugs are often faulty. Science, 1997. vol. 278, pp. 1041-1042.*
Seaver. Monoclonal antibodies in industry: more difficult than originally thought. Genetic Engineering, 1994. vol. 14, pp. 10 and 21.*
Qing, Shuo, Zhihua, Huifen, Ping, Lijiang, Xiaorong, Liming, Daiwen, Yu, Wei, Min, Zuohua, and Guanxin. The in vitro antitumor effect and in vivo tumor specificity distribution of human mouse chimeric antibody against transferrin receptor. Cancer Immunology and Immunotherapy, 2006. vol. 55, pp. 1111-1121.*
Lesley and Schulte. Inhibition of cell growth by monoclonal antitransferrin receptor antibodies. Molecular and Cellular Biology, 1985. vol. 5, p. 1814-1821.*
Moura, Lepelletier, Amulf, England, Baude, Beaumont, Bazarbachi, Benhamou, Monteiro, and Hermine. A neutralizing monoclonal antibody (mAB A24) directed against the transferrin receptor induces apoptosis of tumor T lymphocytes from ATL patients. Blood, 2004. vol. 103, pp. 1838-1845.*
Ng, Cruz, Sorour, Stinebaugh, Shin, Shin, Morrison, and Penichet. An anti-transferrin receptor avidin fusion protein exhibits both strong proapoptotic activity and the ability to deliver various molecules into cancer cells. Proceedings of the National Academy of Sciences, 2002. vol. 99, pp. 10706-10711.*
Shinohara, Fan, Ozawa, Yano, Van Arsdell, Viner, Beers, Pastan, and Fidler. Site specific expression of transferrin receptor by human colon cancer cells directly correlated with eradication by antitransferrin recombinant immunotoxin. International Journal of Oncology, 2000. vol. 17, pp. 643-651.*
Taetle, Castagnola, and Mendelsohn. Mechanisms of growth inhibition by anti-transferrin receptor monoclonal antibodies. Cancer Research, 1986. vol. 46, pp. 1759-1763.*
Batra et al., "Antitumor activity in mice of an immunotoxin made with anti-transferrin receptor and a recombinant form of *Pseudomonas* exotoxin," Proceedings of the National Academy of Sciences of the United States of America, Nov. 1989, vol. 86, No. 21, pp. 8545-8549.
Brooks et al., "Phase la trial of murine immunoglobulin A antitransferrin receptor antibody 42/6," Clinical Cancer Research: An Official Journal of the American Association for Cancer Research, Nov. 1995, vol. 1, No. 11, pp. 1259-1265.
Van Dijk et al., "Selective Depletion of Major and Mino Histocompatibility Antigen Reactive T Cells: Towards Prevention of Acute Graft-Versus-Host Disease," British Journal of Haematology, Oxford GB, Oct. 1999, vol. 107, No. 1, pp. 169-175.
Jones et al., "Depletion of CD25 Regulatory Cells Results in Suppression of Melanoma Growth and Induction of Autoreactivity in Mice," Cancer Immunity, XX, XX, Feb. 2002, vol. 2, No. 22, pp. 1-12.
Rammensee et al., "Antibodies Against the Transferrin Receptor Block the Induction of the Cytotoxic T Lymphocytes a New Method for Antigen-Specific Negative Selection In-Vitro," European Journall of Immunology, 1985, vol. 15, No. 7, pp. 687-692.
Taetle et al., "Effects of Monoclonal Anti-Transferrin Receptor Antibodies on In-Vitro Growth of Human Solid Tumor Cells," Cancer Research, American Association for Cancer Research, Apr. 1987, vol. 47, No. 8, pp. 2040-2044.
Weissman et al., "Exposure of K562 Cells to Anti-Receptor Monoclonal Antibody OKT9 Results in Rapid Redistribution and Enhanced Degradation of the Transferrin Receptor," Journal of Cell Biology, Rockefeller University Press, New York, US, 1986, vol. 102, No. 3, pp. 951-958.

(Continued)

*Primary Examiner* — Misook Yu
*Assistant Examiner* — Julie Wu
(74) *Attorney, Agent, or Firm* — Foley & Lardner LLP

(57) ABSTRACT

The present invention provides novel anti-CD71 monoclonal antibodies, in particular mouse-human chimeric anti-CD71 monoclonal antibodies, advantageously associated to effector cells for triggering ADCC mechanisms. Anti-CD71 antibodies, as well as pharmaceutical compositions containing them, are useful for inhibiting proliferation and/or killing malignant tumour cells, especially metastatic cutaneous and uveal melanoma cells.

5 Claims, 6 Drawing Sheets

OTHER PUBLICATIONS

White et al., "Combinations of anti-transferrin receptor monoclonal antibodies inhibit human tumor cell growth in vitro and in vivo: evidence for synergistic antiproliferative effects," Cancer Research, Oct. 1990, vol. 50. No. 19, pp. 6295-6301.

International Search Report for Appln. No. PCT/IB2006/002331 dated Mar. 14, 2007; 5 pages.
US 6,290,956, 09/2001, Bander (withdrawn)

* cited by examiner

Amino acid sequence (SEQ ID No.1) and nucleotide sequence (SEQ ID No.3) of the variable region of the heavy chain of the mouse anti-CD71 antibody   BA120g

```
          Signal peptide
1/1                                    31/11
ATG GAG TTC GGC CTG AGC TGG CTG TTC CTG GTG GCT ATT CTT AAG GGT GTC CAG TGT GAG
 M   E   F   G   L   S   W   L   F   L   V   A   I   L   K   G   V   Q   C   E
61/21                                  91/31
GTT CAG CTC CAG CAG TCT GGG ACT GTG CTG GCA AGG CCT GGG GCT TCC GTG AAG ATG TCC
 V   Q   L   Q   Q   S   G   T   V   L   A   R   P   G   A   S   V   K   M   S
121/41                                 151/51
TGC AAG GCT TCT GGC TAC AGT TTT ACC ATC TAC TGG ATA CAC TGG GTA AAA CAG AGG CCT
 C   K   A   S   G   Y   S   F   T   I   Y   W   I   H   W   V   K   Q   R   P
181/61                                 271/91
GGA CAG GGT CTA GAA TGG ATT GCT ACT ATT TAT CCT GGG AAT AGT GAT ATT ATT TAC AAC
 G   Q   G   L   E   W   I   A   T   I   Y   P   G   N   S   D   I   I   Y   N
301/101                                333/111
CAG AAG TTC AAG GGC AAG GCC AAA CTG ACT GCG GTC ACA TCC GCC AGC ACT GCC TAC ATG
 Q   K   F   K   G   K   A   K   L   T   A   V   T   S   A   S   T   A   Y   M
361/121                                391/131
GAG CTC AGC AGC CTG ACA AAT GAG GCC TCT GCG GTC TAT TAC TGT ACA AGA CAG GGG TAC
 E   L   S   S   L   T   N   E   A   S   A   V   Y   Y   C   T   R   Q   G   Y
421/141                                451/151
GAT TAT TAT GCT ATG GAC TAT TGG GGT CAA GGA ACC TCA GTC ACC GTC TCC TCA
 D   Y   Y   A   M   D   Y   W   G   Q   G   T   S   V   T   V   S   S
```

FIG 4

Amino acid sequence (SEQ ID No.5) and nucleotide sequence (SEQ ID No.7) of the constant region of the heavy chain of human gamma 1 immunoglobulins

```
1/1                                          31/11
GCT AGC ACC AAG GGC CCA TCG GTC TTC CCC CTG GCA CCC TCC TCC AAG AGC ACC TCT GGG
 A   S   T   K   G   P   S   V   F   P   L   A   P   S   S   K   S   T   S   G
61/21                                        91/31
GGC ACA GCG GCC CTG GGC TGC CTG GTC AAG GAC TAC TTC CCC GAA CCG GTG ACG GTG TCG
 G   T   A   A   L   G   C   L   V   K   D   Y   F   P   E   P   V   T   V   S
121/41                                       151/51
TGG AAC TCA GGC GCC CTG ACC AGC GGC GTG CAC ACC TTC CCG GCT GTC CTA CAG TCC TCA
 W   N   S   G   A   L   T   S   G   V   H   T   F   P   A   V   L   Q   S   S
181/61                                       211/71
GGA CTC TAC TCC CTC AGC AGC GTG GTG ACC GTG CCC TCC AGC AGC TTG GGC ACC CAG ACC
 G   L   Y   S   L   S   S   V   V   T   V   P   S   S   S   L   G   T   Q   T
241/81                                       271/91
TAC ATC TGC AAC GTG AAT CAC AAG CCC AGC AAC ACC AAG GTG GAC AAG AAA GTt GAG CCC
 Y   I   C   N   V   N   H   K   P   S   N   T   K   V   D   K   K   V   E   P
301/101                                      331/111
AAA TCT TGT GAC AAA ACT CAC ACA TGC CCA CCG TGC CCA GCA CCT GAA CTC CTG GGG GGA
 K   S   C   D   K   T   H   T   C   P   P   C   P   A   P   E   L   L   G   G
361/121                                      391/131
CCG TCA GTC TTC CTC TTC CCC CCA AAA CCC AAG GAC ACC CTC ATG ATC TCC CGG ACC CCT
 P   S   V   F   L   F   P   P   K   P   K   D   T   L   M   I   S   R   T   P
421/141                                      451/151
GAG GTC ACA TGC GTG GTG GTG GAC GTG AGC CAC GAA GAC CCT GAG GTC AAG TTC AAC TGG
 E   V   T   C   V   V   V   D   V   S   H   E   D   P   E   V   K   F   N   W
481/161                                      511/171
TAC GTG GAC GGC GTG GAG GTG CAT AAT GCC AAG ACA AAG CCG CGG GAG GAG CAG TAC AAC
 Y   V   D   G   V   E   V   H   N   A   K   T   K   P   R   E   E   Q   Y   N
541/181                                      571/191
AGC ACG TAC CGt GTG GTC AGC GTC CTC ACC GTC CTG CAC CAG GAC TGG CTG AAT GGC AAG
 S   T   Y   R   V   V   S   V   L   T   V   L   H   Q   D   W   L   N   G   K
601/201                                      631/211
GAG TAC AAG TGC AAG GTC TCC AAC AAA GCC CTC CCA GCC CCC ATC GAG AAA ACC ATC TCC
 E   Y   K   C   K   V   S   N   K   A   L   P   A   P   I   E   K   T   I   S
661/221                                      691/231
AAA GCC AAA GGG CAG CCC CGA GAA CCA CAG GTG TAC ACC CTG CCC CCA TCC CGG GAT GAG
 K   A   K   G   Q   P   R   E   P   Q   V   Y   T   L   P   P   S   R   D   E
721/241                                      751/251
CTG acc AAG AAC CAG GTC AGC CTG ACC TGC CTG GTC AAA GGC TTC TAT CCC AGC GAC ATC
 L   T   K   N   Q   V   S   L   T   C   L   V   K   G   F   Y   P   S   D   I
781/261                                      811/271
GCC GTG GAG TGG GAG AGC AAT GGG CAG CCG GAG AAC AAC TAC AAG ACC ACG CCT CCC GTG
 A   V   E   W   E   S   N   G   Q   P   E   N   N   Y   K   T   T   P   P   V
841/281                                      871/291
CTG GAC TCC GAC GGC TCC TTC TTC CTC TAC AGC AAG CTC ACC GTG GAC AAG AGC AGG TGG
 L   D   S   D   G   S   F   F   L   Y   S   K   L   T   V   D   K   S   R   W
901/301                                      931/311
CAG CAG GGG AAC GTC TTC TCA TGC TCC GTG ATG CAT GAG GCT CTG CAC AAC CAC TAC ACG
 Q   Q   G   N   V   F   S   C   S   V   M   H   E   A   L   H   N   H   Y   T
961/321
CAG AAG AGC CTC TCC CTG TCT CCG GGT AAA
 Q   K   S   L   S   L   S   P   G   K
```

FIG 5

Amino acid sequence (SEQ ID No.2) and nucleotide sequence (SEQ ID No.4) of the variable region of the light chain of the mouse anti-CD71 antibody BA120g

```
          Signal peptide
1/1                              31/11
ATG GAC ATG CGT GTG CCC GCT CAA CTC CTG GGC CTG CTG CTG CTC TGG CTC CCA GGT GCG
 M   D   M   R   V   P   A   Q   L   L   G   L   L   L   L   W   L   P   G   A
61/21                            91/31
CGC TGT GAT GTC CAG ATA ACC CAG TCT CCA TCT TAT CTT GCT GCA TCT CCT GGA GAA ACC
 R   C   D   V   Q   I   T   Q   S   P   S   Y   L   A   A   S   P   G   E   T
121/41                           151/51
ATC ATT ATT AAT TGC AGG GCA AGT AAG AGC ATT AGC AAA TAT TTA GCC TGG TAT CAA GAG
 I   I   I   N   C   R   A   S   K   S   I   S   K   Y   L   A   W   Y   Q   E
181/61                           271/91
AAA CCT GGG AAA ACT AAT AAG CTT CTT ATC TAC TCT GGA TCC ACT TTG CAA TCT GGA ATT
 K   P   G   K   T   N   K   L   L   I   Y   S   G   S   T   L   Q   S   G   I
301/101                          333/111
CCA TCA AGG TTC AGT GGC AGT GGA TCT GGT ACA GAT TTC ACT CTC ACC ATC AGT AGC CTG
 P   S   R   F   S   G   S   G   S   G   T   D   F   T   L   T   I   S   S   L
361/121                          391/131
GAG CCT CAA GAT TTT GCA ATG TAT TAC TGT CAA CAG CAT AAT GAA TAC CCG TGG ACG TTC
 E   P   Q   D   F   A   M   Y   Y   C   Q   Q   H   N   E   Y   P   W   T   F
421/141                          451/151
GGT GGA GGC ACC AAG CTG GAA ATC AAA CGG
 G   G   G   T   K   L   E   I   K   R
```

FIG 6A

Amino acid sequence (SEQ ID No.11) and nucleotide sequence (SEQ ID No.12) of the variable region of the alternative light chain of the mouse anti-CD71 antibody BA120g

```
             10        20        30        40        50        60
1     AACATTGTAATGACCCAATCTCCCAAATCCATGTCCATGTCAGTAGGAGAGAGGGTCACC
1       N  I  V  M  T  Q  S  P  K  S  M  S  M  S  V  G  E  R  V  T 70        80        90       100       110       120
61    TTGACCTGCAAGGCCAGTGAGAATGTGGTTACTTATGTTTCCTGGTATCAACAGAAACCA
21      L  T  C  K  A  S  E  N  V  V  T  Y  V  S  W  Y  Q  Q  K  P 130       140       150       160       170       180
121   GAGCAGTCTCCTAAACTGCTGATATACGGGGCATCCAACCGGTACACTGGGGTCCCCGAT
41      E  Q  S  P  K  L  L  I  Y  G  A  S  N  R  Y  T  G  V  P  D 190       200       210       220       230       240
181   CGCTTCACAGGCAGTGGATCTGCAACAGATTTCACTCTGACCATCAGCAGTGTGCAGGCT
61      R  F  T  G  S  G  S  A  T  D  F  T  L  T  I  S  S  V  Q  A 250       260       270       280       290       300
241   GAAGACCTTGCAGATTATCACTGTGGACAGGGTTACAGCTATCCGTACACGTTCGGAGGG
81      E  D  L  A  D  Y  H  C  G  Q  G  Y  S  Y  P  Y  T  F  G  G 310       320
301   GGGACCAAGCTGGAAATAAAACGG
101     G  T  K  L  E  I  K  R
```

FIG 6B

Amino acid sequence (SEQ ID No.6) and nucleotide sequence (SEQ ID No.8) of the constant region of the light chain of human Kappa immunoglobulins

```
1/1                             31/11
ACg GTG GCT GCA CCA TCT GTC TTC ATC TTC CCG CCA TCT GAT GAG CAG TTG AAA TCT GGA
thr val ala ala pro ser val phe ile phe pro pro ser asp glu gln leu lys ser gly
61/21                           91/31
ACT GCC TCT GTT GTG TGC CTG CTG AAT AAC TTC TAT CCC AGA GAG GCC AAA GTA CAG TGG
thr ala ser val val cys leu leu asn asn phe tyr pro arg glu ala lys val gln trp
121/41                          151/51
AAG GTG GAT AAC GCC CTC CAA TCG GGT AAC TCC CAG GAG AGT GTC ACA GAG CAG GAC AGC
lys val asp asn ala leu gln ser gly asn ser gln glu ser val thr glu gln asp ser
181/61                          211/71
AAG GAC AGC ACC TAC AGC CTC AGC AGC ACC CTG ACG CTG AGC AAA GCA GAC TAC GAG AAA
lys asp ser thr tyr ser leu ser ser thr leu thr leu ser lys ala asp tyr glu lys
241/81                          271/91
CAC AAA GTC TAC GCC TGC GAA GTC ACC CAT CAG GGC CTG AGt TCG CCC GTC ACA AAG AGC
his lys val tyr ala cys glu val thr his gln gly leu ser ser pro val thr lys ser
301/101
TTC AAC AGG GGA GAG TGT
phe asn arg gly glu cys
```

FIG 7

Amino acid sequence (SEQ ID No.9) and nucleotide sequence (SEQ ID No.10) of the constant region of the heavy chain of human gamma 4 immunoglobulins (GENBANK n° BC025985)

```
1/1                                              31/11
GCT TCC ACC AAG GGC CCA TCC GTC TTC CCC CTG GCG CCC TGC TCC AGG AGC ACC TCC GAG
 A   S   T   K   G   P   S   V   F   P   L   A   P   C   S   R   S   T   S   E
61/21                                            91/31
AGC ACA GCg GCC CTG GGC TGC CTG GTC AAG GAC TAC TTC CCC GAA CCG GTG ACG GTG TCG
 S   T   A   A   L   G   C   L   V   K   D   Y   F   P   E   P   V   T   V   S
121/41                                           151/51
TGG AAC TCA GGC GCC CTG ACC AGC GGC GTG CAC ACC TTC CCG GCT GTC CTA CAG TCC TCA
 W   N   S   G   A   L   T   S   G   V   H   T   F   P   A   V   L   Q   S   S
181/61                                           211/71
GGA CTC TAC TCC CTC AGC AGC GTG GTG ACC GTG CCC TCC AGC AGC TTG GGC ACG AAG ACC
 G   L   Y   S   L   S   S   V   V   T   V   P   S   S   S   L   G   T   K   T
241/81                                           271/91
TAC ACC TGC AAt GTA GAT CAC AAG CCC AGC AAC ACC AAG GTG GAC AAG AGA GTT GAG TCC
 Y   T   C   N   V   D   H   K   P   S   N   T   K   V   D   K   R   V   E   S
301/101                                          331/111
AAA TAT GGT CCC CCA TGC CCA TCA TGC CCA GCA CCT GAG TTC CTG GGG GGA CCA TCA GTC
 K   Y   G   P   P   C   P   S   C   P   A   P   E   F   L   G   G   P   S   V
361/121                                          391/131
TTC CTG TTC CCC CCA AAA CCC AAG GAC ACT CTC ATG ATC TCC CGG ACC CCT GAG GTC ACG
 F   L   F   P   P   K   P   K   D   T   L   M   I   S   R   T   P   E   V   T
421/141                                          451/151
TGC GTG GTG GTG GAC GTG AGC CAG GAA GAC CCC GAG GTC CAG TTC AAC TGG TAC GTG GAT
 C   V   V   V   D   V   S   Q   E   D   P   E   V   Q   F   N   W   Y   V   D
481/161                                          511/171
GGC GTG GAG GTG CAT AAT GCC AAG ACA AAG CCG CGG GAG GAG CAG TTC AAC AGC ACG TAC
 G   V   E   V   H   N   A   K   T   K   P   R   E   E   Q   F   N   S   T   Y
541/181                                          571/191
CGT GTG GTC AGC GTC CTC ACC GTC CTG CAC CAG GAC TGG CTG AAC GGC AAG GAG TAC AAG
 R   V   V   S   V   L   T   V   L   H   Q   D   W   L   N   G   K   E   Y   K
601/201                                          631/211
TGC AAG GTC TCC AAC AAA GGC CTC CCG TCC TCC ATC GAG AAA ACC ATC TCC AAA GCC AAA
 C   K   V   S   N   K   G   L   P   S   S   I   E   K   T   I   S   K   A   K
661/221                                          691/231
GGG CAG CCC CGA GAG CCA CAG GTG TAC ACC CTG CCC CCA TCC CAG GAG GAG ATG ACC AAG
 G   Q   P   R   E   P   Q   V   Y   T   L   P   P   S   Q   E   E   M   T   K
721/241                                          751/251
AAC CAG GTC AGC CTG ACC TGC CTG GTC AAA GGC TTC TAC CCC AGC GAC ATC GCC GTG GAG
 N   Q   V   S   L   T   C   L   V   K   G   F   Y   P   S   D   I   A   V   E
781/261                                          811/271
TGG GAG AGC AAT GGG CAG CCG GAG AAC AAC TAC AAG ACC ACG CCT CCC GTG CTG GAC TCC
 W   E   S   N   G   Q   P   E   N   N   Y   K   T   T   P   P   V   L   D   S
841/281                                          871/291
GAC GGC TCC TTC TTC CTC TAC AGC AGG CTA ACC GTG GAC AAG AGC AGG TGG CAG GAG GGG
 D   G   S   F   F   L   Y   S   R   L   T   V   D   K   S   R   W   Q   E   G
901/301                                          931/311
AAT GTC TTC TCA TGC TCC GTG ATG CAT GAG GCT CTG CAC AAC CAC TAC ACA CAG AAG AGC
 N   V   F   S   C   S   V   M   H   E   A   L   H   N   H   Y   T   Q   K   S
961/321
CTC TCC CTG TCT CTG GGT AAA
 L   S   L   S   L   G   K
```

Underlined : two silent mutations

FIG 8

SEQUENCE LISTING

<160> NUMBER OF SEQ ID NOS: 12

<210> SEQ ID NO 1
<211> LENGTH: 138
<212> TYPE: PRT
<213> ORGANISM: Mus musculus

<400> SEQUENCE: 1

Met Glu Phe Gly Leu Ser Trp Leu Phe Leu Val Ala Ile Leu Lys Gly
1               5                   10                  15

Val Gln Cys Glu Val Gln Leu Gln Gln Ser Gly Thr Val Leu Ala Arg
                20                  25                  30

Pro Gly Ala Ser Val Lys Met Ser Cys Lys Ala Ser Gly Tyr Ser Phe
            35                  40                  45

Thr Ile Tyr Trp Ile His Trp Val Lys Gln Arg Pro Gly Gln Gly Leu
        50                  55                  60

Glu Trp Ile Ala Thr Ile Tyr Pro Gly Asn Ser Asp Ile Ile Tyr Asn
65                  70                  75                  80

Gln Lys Phe Lys Gly Lys Ala Lys Leu Thr Ala Val Thr Ser Ala Ser
                85                  90                  95

Thr Ala Tyr Met Glu Leu Ser Ser Leu Thr Asn Glu Ala Ser Ala Val
            100                 105                 110

Tyr Tyr Cys Thr Arg Gln Gly Tyr Asp Tyr Tyr Ala Met Asp Tyr Trp
            115                 120                 125

Gly Gln Gly Thr Ser Val Thr Val Ser Ser
            130                 135

<210> SEQ ID NO 2
<211> LENGTH: 130
<212> TYPE: PRT
<213> ORGANISM: Mus musculus

<400> SEQUENCE: 2

Met Asp Met Arg Val Pro Ala Gln Leu Leu Gly Leu Leu Leu Leu Trp
1               5                   10                  15

Leu Pro Gly Ala Arg Cys Asp Val Gln Ile Thr Gln Ser Pro Ser Tyr
                20                  25                  30

Leu Ala Ala Ser Pro Gly Glu Thr Ile Ile Ile Asn Cys Arg Ala Ser
            35                  40                  45

Lys Ser Ile Ser Lys Tyr Leu Ala Trp Tyr Gln Glu Lys Pro Gly Lys
        50                  55                  60

Thr Asn Lys Leu Leu Ile Tyr Ser Gly Ser Thr Leu Gln Ser Gly Ile
65                  70                  75                  80

Pro Ser Arg Phe Ser Gly Ser Gly Ser Gly Thr Asp Phe Thr Leu Thr
                85                  90                  95

Ile Ser Ser Leu Glu Pro Gln Asp Phe Ala Met Tyr Tyr Cys Gln Gln
            100                 105                 110

His Asn Glu Tyr Pro Trp Thr Phe Gly Gly Gly Thr Lys Leu Glu Ile
            115                 120                 125

Lys Arg
    130

<210> SEQ ID NO 3
<211> LENGTH: 414
<212> TYPE: DNA
<213> ORGANISM: Mus musculus

<400> SEQUENCE: 3
atggagttcg gcctgagctg ctgttcctg gtggctattc ttaagggtgt ccagtgtgag      60
gttcagctcc agcagtctgg gactgtgctg gcaaggcctg ggcttccgt gaagatgtcc     120 tgcaaggctt ctggctacag ttttaccatc tactggatac actgggtaaa acagaggcct    180
ggacagggtc tagaatggat tgctactatt atcctgggaa atagtgatat tatttacaac    240
cagaagttca agggcaaggc caaactgact gcggtcacat ccgccagcac tgcctacatg    300

```
gagctcagca gcctgacaaa tgaggcctct gcggtctatt actgtacaag acaggggtac    360
gattattatg ctatggacta ttggggtcaa ggaacctcag tcaccgtctc ctca          414
```

<210> SEQ ID NO 4
<211> LENGTH: 390
<212> TYPE: DNA
<213> ORGANISM: Mus musculus

<400> SEQUENCE: 4

```
atggacatgc gtgtgcccgc tcaactcctg ggcctgctgc tgctctggct cccaggtgcg     60
cgctgtgatg tccagataac ccagtctcca tcttatcttg ctgcatctcc tggagaaacc    120
atcattatta attgcagggc aagtaagagc attagcaaat atttagcctg gtatcaagag    180
aaacctggga aaactaataa gcttcttatc tactctggat ccactttgca atctggaatt    240
ccatcaaggt tcagtggcag tggatctggt acagatttca ctctcaccat cagtagcctg    300
gagcctcaag attttgcaat gtattactgt caacagcata tgaatacccc gtggacgttc    360
ggtggaggca ccaagctgga aatcaaacgg                                      390
```

<210> SEQ ID NO 5
<211> LENGTH: 330
<212> TYPE: PRT
<213> ORGANISM: homo sapiens

<400> SEQUENCE: 5

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 106
<212> TYPE: PRT
<213> ORGANISM: homo sapiens

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 7
<211> LENGTH: 990
<212> TYPE: DNA
<213> ORGANISM: homo sapiens

<400> SEQUENCE: 7
gctagcacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
```

```
gccgtggagt gggagagcaa tgggcagccg agaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

```
<210> SEQ ID NO 8
<211> LENGTH: 318
<212> TYPE: DNA
<213> ORGANISM: homo sapiens

<400> SEQUENCE: 8
acggtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gttcgcccgt cacaaagagc    300
ttcaacaggg gagagtgt                                                  318
```

```
<210> SEQ ID NO 9
<211> LENGTH: 327
<212> TYPE: PRT
<213> ORGANISM: homo sapiens

<400> SEQUENCE: 9

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
           100                 105                 110

Glu Phe Leu Gly Gly Pro Ser Val Phe Leu Phe Pro Pro Lys Pro Lys
       115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 981
<212> TYPE: DNA
<213> ORGANISM: homo sapiens

<400> SEQUENCE: 10

```
gcttccacca agggcccatc cgtcttcccc ctggcgccct gctccaggag cacctccgag    60
agcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca atgtagatca caagcccagc aacaccaagg tggacaagag agttgagtcc   300
aaatatggtc ccccatgccc atcatgccca gcacctgagt tcctgggggg accatcagtc   360
ttcctgttcc cccaaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggctcct tcttcctcta cagcaggcta accgtggaca agagcaggtg gcaggagggg   900
aatgtcttct catgctccgt gatgcatgag gctctgcaca accactacac acagaagagc   960
ctctccctgt ctctgggtaa a                                             981
```

<210> SEQ ID NO 11
<211> LENGTH: 108
<212> TYPE: PRT
<213> ORGANISM: Mus musculus

<400> SEQUENCE: 11

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

```
Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Gly Tyr Ser Tyr Pro Tyr
                 85                  90                  95

Thr Phe Gly Gly Gly Thr Lys Leu Glu Ile Lys Arg
            100                 105

<210> SEQ ID NO 12
<211> LENGTH: 324
<212> TYPE: DNA
<213> ORGANISM: Mus musculus

<400> SEQUENCE: 12
aacattgtaa tgacccaatc tcccaaatcc atgtccatgt cagtaggaga gagggtcacc      60
ttgacctgca aggccagtga gaatgtggtt acttatgttt cctggtatca acagaaacca    120
gagcagtctc ctaaactgct gatatacggg gcatccaacc ggtacactgg ggtcccggat    180
cgcttcacag gcagtggatc tgcaacagat ttcactctga ccatcagcag tgtgcaggct    240
gaagaccttg cagattatca ctgtggacag ggttacagct atccgtacac gttcggaggg    300
gggaccaagc tggaaataaa acgg                                          324
```

ANTI-CD71 MONOCLONAL ANTIBODIES AND USES THEREOF FOR TREATING MALIGNANT TUMOR CELLS

CROSS-REFERENCE TO RELATED APPLICATIONS

This application is the U.S. national stage application of PCT/IB2006/002331, filed Jun. 14, 2006, which is a continuation of U.S. application Ser. No. 11/154,262, filed Jun. 15, 2005 now U.S. Pat. No. 7,736,647. Each application is hereby incorporated in their entirety.

The present invention provides novel anti-CD71 monoclonal antibodies, in particular mouse-human chimeric anti-CD71 monoclonal antibodies, advantageously associated to effector cells for triggering ADCC mechanisms. Anti-CD71 antibodies, as well as pharmaceutical compositions containing them, are useful for inhibiting proliferation and/or killing malignant tumour cells, especially metastatic cutaneous and uveal melanoma cells.

Monoclonal antibodies can influence tumour cell survival by several mechanisms, acting directly on the tumor target cells and/or by activation of effector mechanisms mediated by soluble factors or cells. Originally, antibody was of murine origin and, when administered to humans, induced strong immune responses to the foreign mouse immunoglobulin. This limited their use. Genetic engineering has enabled the development of so-called humanized antibodies with increased therapeutic efficacy.

Chimeric antibodies are 65-90% human nucleotides sequences and consist of the murine variable regions, which bring about antigen recognition, fused to the constant or effector part of a human antibody. Humanized antibodies are about 95% human, and are made by grafting only the hypervariable region, or complementarity-determining regions, of the murine antibody—which determines antibody specificity—onto a human antibody backbone. The developments of genetically engineered transgenic mice and advances in the generation of synthetic human antibody libraries have enabled the production of fully human antibodies on a commercial scale.

Chimeric, humanized, and fully human antibodies have less immunogenicity than early antibody constructs and allow repeated antibody administration, an improved capacity to recruit cytotoxic cells and complement, and an increased stability in the circulatory system. These improvements have contributed to the increased therapeutic efficiency of monoclonal antibodies. Small antibody fragments have also been engineered to improve antibody penetration into bulky avascular tumours, especially solid tumours. A single-chain fixed-variable (Fv) region consists of only one heavy-chain variable domain and one light-chain variable domain, which are covalently linked by a short peptide linker. These fragments can be used to deliver radioisotopes or drugs to tumour sites. Antibodies have also been designed that have two different antigen-binding arms and hence have dual-binding specificity. An example is when one arm binds to the tumour cell and the other binds to the effector cell. Another example is when the arms bind not only to two different antigens on the tumor cell, but also to the effector cell by their Fc fragment. These constructs increase antibody-mediated tumour-cell killing through the recruitment of host immune-effector cells (T cells, natural-killer cells, and macrophages).

Many antigens that are recognized by monoclonal antibodies are expressed not only by malignant cells, but also by at least one subset of healthy adult cells. The best target antigen for a monoclonal antibody (mAb) therapy would be one that is both stably and homogeneously expressed by all tumour cells, is not or hardly expressed by normal tissues, does not exist under a soluble form (to avoid rapid antibody clearance), and is easily accessible to the monoclonal antibody.

Unlabelled antibodies cause tumor cells to die or to stop their proliferation through a combination of different mechanisms: 1) recruitment and activation of effector cells by antibody-dependent cell-mediated cytotoxicity (ADCC), by complement-dependent cytotoxicity (CDC), 2) blocking of receptor-ligand interactions and prevention of growth factor activity, 3) induction of apoptosis, and 4) secretion of cytokines.

Some antibodies do not induce cell death by themselves and instead are used to deliver radioisotopes, toxins, enzymes, or drugs to tumour sites. Specific targeting of cytotoxic agents to tumour cells has the potential to reach high concentrations at tumour sites, without the dose-limiting side-effects of systemic administration. In that context, antibodies that target antigens that are rapidly internalized offer another advantage.

Radioimmunoconjugates selectively deliver radiation to tumor sites. In terms of radionuclides, one may use, for instance, $I^{131}$ or $Y^{90}$, as well as new β (212 Pb, mixte βγ 177 Lu, 153 Sm, 186 Re, 67 Cu, 225 Ac . . . ) or α (213 Bi, 211 At . . . ) emitters, advantageously using improved chelation technologies such as MX-DTPA, CHX-A" DPA, C-DOTA, PA-DOTA, DOTA-NCS (2-p-isothiocyanatobenzyl-1,4,7,10-tetraazacyclododecane-1,4,7,10-tetracetic acid). The cytotoxicity depends on the pharmacokinetics of antibody isolation and retention of the radionuclide. Healthy tissues, especially bone marrow, are also irradiated because of strong emission energies.

Alpha chains of plant and bacterial toxins (such as ricin, diphtheria toxin, or pseudomonas toxin) can be directly attached to monoclonal antibodies. After binding and internalization in the cell, these toxins disrupt protein synthesis at low concentrations. These toxins also commonly elicit strong immune responses in humans, which limits their repeated use.

Drugs such as doxorubicin and calicheamicin can be directly attached to monoclonal antibodies. Antibody-mediated delivery with calicheamicin allows clinical use of this highly potent agent, which would otherwise be too toxic for systemic administration on its own.

For reviews on these aspects, see M. Harris (2004), and Cancer Highlights (2004).

CD71 is a type II glycoprotein which exists as an homodimer of 180 kDa, linked by a disulfide bond in position Cys89. This glycoprotein is acylated at Cystein 62 and phosphorylated at Serine 24 by protein kinase C. It contains an internalization signal constituted by a tetrapeptide YTRF (amino acids 20-23) (Collawn et al, 1993). Upon cleavage between Arg 100 and Leu 101 by a yet unknown protease, CD71 becomes soluble. O-glycosilation at Thr 104 reduces the sensitivity of CD71 to cleavage. Mammalian and chicken transferrin receptors have an RGD sequence, suggesting a possible evolutionary relationship with adhesion molecules. In terms of sequence homology, there is an homology with the C5a streptococcal peptidase sequence and with the PSA sequence (Prostate Specific Antigen, which is not prostate-specific but which exhibits a type II acid dipeptidase activity). A ligand of CD71 is the transferrin, protein responsible for iron transport. Recently, it has been shown that CD71 is also a receptor for IgA (Haddad et al, 2003).

Ferrotransferrin binds to CD71 under neutral pH and is internalized in the endosomal compartment where the pH is about 5. Iron is released and carried in the cytoplasm by an unknown mechanism. The apotransferrin remains bound to CD71 at pH5 and returns to the cell surface where the pH is about 7.4. Under neutral pH conditions, the apotransferrin has no longer affinity for CD71, allowing thus another cycle to begin. This feature of CD71 permits to use this surface molecule for internalizing a drug, a toxin or a radioelement coupled to an antibody (Lee et al, 2000) (Li et al, 2002) (Ng et al, 2002) (Shinohara et al, 2000). CD71 binds in cis, via a non-covalent binding, to the ζ chain of the TCR, where it may be involved in signal transduction. Moreover, CD71 monomers are supposed to form a complex with integrin CD29/CD49d (VLA4) via a disulfide bond.

CD71 plays an essential role in cell proliferation by controlling iron uptake which is essential in several metabolic pathways. This occurs via the binding and the endocytosis of transferrin. Expression of CD71 is post-transcriptionally regulated through RNA stability; it also depends on iron intracellular levels. The IRE-BP (iron-response element binding protein) exists under two different form, IRP-1 and IRP-2. IRP-1 is similar to the mitochondrial aconitase, whereas no aconitase activity has yet been described for IRP-2, which is however structurally homologous to aconitase. In case of iron deficiency, IRP-1 and IRP-2 stabilize the CD71 RNA by binding to specific sequences designated IREs (iron response elements located in the untranslated 3' region of the RNA). When the level of iron is high, the IRE-BP affinity for IREs is low and the RNA is more sensitive to degradation. In addition, nitric oxide modifies CD71 expression by activating the binding of IRE-BP and by stabilizing the RNA.

CD71 is almost undetectable on leucocytes and resting cells. This expression is up-regulated by cell activation and proliferation. For these reasons, CD71 appears to be a target of choice for treating a number of tumors. Nevertheless, in the red blood cell line, red blood cell precursors and reticulocytes express CD71. This is also deduced from mice lacking the CD71 transferrin receptor, which have a severe phenotype affecting both erythropoiesis and neurologic development (Levy et al., 1999). This was also shown in human in a case of an acquired iron-deficiency-anemia by Larrick J. W. and Hyman E. S., 1984. On the contrary, this showed that stem cells do not express CD71, confirming that an anti-CD71 antibody may be useful for anti-tumoral therapy (Zech et al, 2003). Besides, CD71 is expressed on the cerebral endothelium and this enables drugs to go through the blood-brain barrier, especially for treating gliomas (Lee et al, 2001). Finally, this last property, if deleterious under given circumstances, can be inhibited upon simultaneous administration of chloroquine.

Metastatic melanoma is a tumor with very poor prognosis, whose incidence is increasing due to modern life style and to prolonged, repeated and unprotected exposure to the sun. At least about 6000 new cases are reported per year in France, with an incidence of 9/100,000 inhabitants in Paris and its region. One third of these cases occur when the subject is less than 40 years old. The prognosis is closely related to the depth of the initial tumor and it results in death in about 100% of the cases of metastatic melanoma. Since more than 20 years, various therapies, either conventional or more innovative, have been tested, but they neither modified the prognosis nor changed the fatal outcome of metastatic melanoma. Despite a better general knowledge, including the identification of tumor antigens and auto-reactive CTL, immunotherapy remains unsuccessful. Immunotherapy has associated in various ways tumoral cell vaccination with tetramer-associated peptides, adjuvants, cytokines or dendritic cells, but has remain inoperative. This may be explained at least in part by a host immunodeficiency (Ugurel S, 2004). Monoclonal antibodies targeting antigens restricted to melanomas such as antigangliosides GD2, GD3, GM2, p97 melanotransferrin, p240 antigen of high molecular weight, have been used (Noronha E J, 1998). Clinical studies have shown that these antibodies can be administered with minimal toxicity. Nevertheless, to date, no antibody, even humanized, chimeric or human (Mills L, 2002), used alone or in combination with a toxin (Shinohara H, 2000), a chimiotherapy, a growth factor such as GM-CFS, IL2 interleukin (Soiffer R J, 1997), TNF or interferon, has proven to be really successful.

More specifically, choroidal and cutaneous melanoma both came from neural crest. Very few people are affected by choroidal metastasis melanoma. These melanomas differ from each other in two points: dissemination mode and the affected organs by metastasis. Thus, choroidal metastasis melanoma dissemination is exclusively by haematogenous way. In more than 90% cases, the first metastasis site (often unique) is hepatic. Few patients will develop other tumoral localisations and a majority of them will die in the nest 6 months after wide hepatic metastasis diagnosis. Cutaneous melanoma presents an evolutionary mode extremely variable and unpredictable because of dissemination is both haematogenous and lymphatic. There is a more specific tropism for the brain although the other organs can be touched. Diagnostic of these two melanomas is mostly made at a localized stage. The associated treatment is then local: it consists of a surgical act or a radiotherapy for the choroidal melanoma and surgical for the cutaneous melanoma.

As mentioned above, it is important to stress that except the surgery and the radiotherapy, conventional therapeutics applied as part of adjuvant treatments or for metastasis disease are very limited in term of efficiency. Moreover, these treatments, requiring prolonged hospitalizations, are painful, heavy and mostly expensive. It thus seems necessary to develop, beside conventional treatments, innovative approaches such as the immunotherapy. The therapeutics, beside local treatments (surgery, chimio- and radiotherapy), are inexistent for choroidal metastasis melanoma and very limited for the cutaneous metastatic melanoma. Therefore, new approaches must be developed to increase the survival of patients affected by metastatic melanoma.

$10^3$ cells from the A375 melanoma cell line were distributed into wells of a 96 flat bottom tissue culture plate at day 0 under 0.1 ml of RPMI 1640 containing antibiotics and 10% Fetal Calf Serum. 5 μg purified monoclonal antibodies to CD101>>BB27>>, or CD2>>O275>>, or CD71>>BA120g>> were added to triplicate wells at the initiation of the culture cells were pulsed with 1 mCi of $^3$H[Tdr] after 2, 3, or 4 days during the last 16 hrs of culture. $^3$H[Tdr] incorporation was measured using a liquid scintillation counter.

Figure 2:
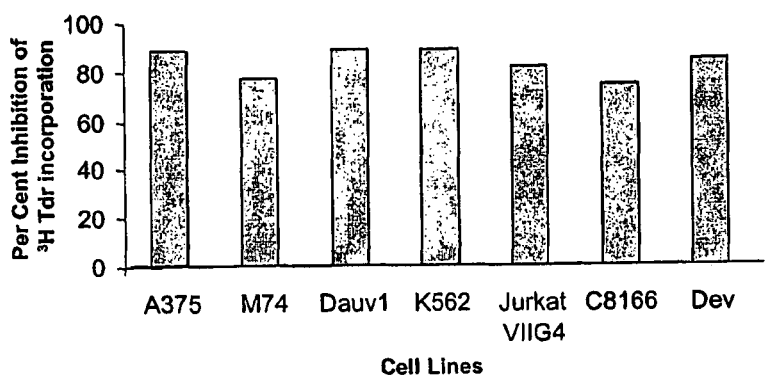

FIG. 2. Inhibitory effects of 25 μg/mL of anti-CD71 monoclonal antibody Ba120G on the proliferation of tumour cell lines in vitro.

Figure 3:
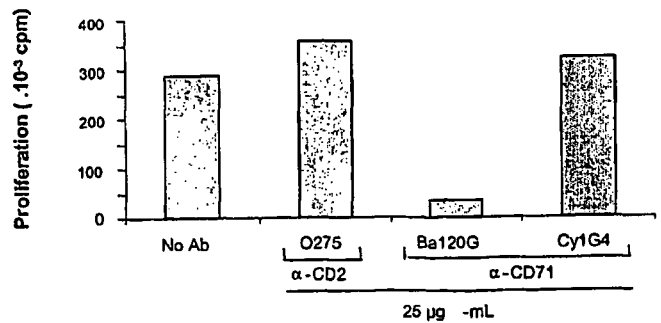

Cell lines used were the three melanoma cell lines A375, M74 and Dauv1, the erythroleukemic cell line K562, the T cell leukemic cell line Jurkat, the HTLV1+ cell line C8166 and the medulloblastoma cell line Dev. Cultures were performed in triplicates. Cells were grown in the presence of 5 μg of purified BA120g or control CD2 mAb during 4 days and then pulsed with 1mCi $^3$H[TdR] during the last 16 hrs of culture. The % inhibition was calculated by making a ratio between the control level of incorporation with isotype matched irrelevant antibody to the level of incorporation with BA120g. Control cpm were 287 989 for A375, 44 740 for M74, 108 389 for Dauv1, 70 519 for K562, 10 655 for Jurkat, 74 292 for C8166 and 179 220 for Dev FIG. 3. Effect of anti-CD71 mAb on A375 cell proliferation.

Purified mAbs to CD2<<O275>> or CD71>>BA120g>> and <<CY1G4>> or no antibody (Ab) were added at 25 µg/mL under 0.2 ml at the initiation of the culture. Cultures of 1000 cells were performed in triplicates. Cells were grown in the presence of 5 µg of purified BA120g or control CD2 mAb during 4 days and then pulsed with 1mCi $^3$H[TdR] during the last 16 hrs of culture.

FIGS. 4 to 8. Nucleotide and amino acid sequences as follows:

FIG. 4: Amino acid sequence (SEQ ID No.1) and nucleotide sequence (SEQ ID No.3) of the variable region of the heavy chain of the mouse anti-CD71 antibody BA120g;

FIG. 5: Amino acid sequence (SEQ ID No.5) and nucleotide sequence (SEQ ID No.7) of the constant region of the heavy chain of human gamma 1 immunoglobulins;

FIGS. 6A and 6B: Amino acid sequences (SEQ ID No.2; SEQ ID No.4) and nucleotide sequences (SEQ ID No.4; SEQ ID No.12) of the variable region of the alternative light chains of the mouse anti-CD71 antibody BA120g;

FIG. 7: Amino acid sequence (SEQ ID No.6) and nucleotide sequence (SEQ ID No.8) of the constant region of the light chain of human Kappa immunoglobulins;

FIG. 8: Amino acid sequence (SEQ ID No.9) and nucleotide sequence (SEQ ID No.10) of the constant region of the heavy chain of human gamma 4 immunoglobulins (GENBANK n° BC025985).

DETAILED DESCRIPTION OF THE PREFERRED EMBODIMENTS

In a first aspect, the present invention concerns an anti-CD71 monoclonal antibody, or a functional fragment thereof, which comprises at least one variable region comprising at least one heavy chain of SEQ ID No. 1 and at least one light chain, the sequence of which is chosen between SEQ ID No. 2 and SEQ ID No. 11.

The term "antibody" is intended to encompass antibodies, digestion fragments, specified portions and variants thereof, including antibody mimetic or comprising portions of antibodies that mimic the structure and/or function of an antibody or specified fragment or portion thereof, including single chain antibodies and fragments thereof.

"Functional fragments" include antigen-binding fragments that bind to a CD71 receptor. For example, antibody fragments capable of binding to CD71 or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

According to another embodiment, the anti-CD71 monoclonal antibody, or the functional fragment thereof, comprises at least one variable region comprising at least one heavy chain encoded by SEQ ID No. 3 and at least one light chain encoded by a sequence chosen between SEQ ID No. 4 and SEQ ID No. 12.

The antibody is preferably produced by a hybridoma cell line designated BA120 and deposited at the Collection Nationale de Cultures de Microorganismes (Institut Pasteur, Paris, France) on Jun. 14, 2005, under number CNCM I-3449.

In a second aspect, the present invention relates to an anti-idiotype antibody, or a functional fragment thereof, which specifically binds at least one anti-CD71 monoclonal antibody as herein described.

Thus, in addition to monoclonal or chimeric anti-CD71 antibodies as described herein, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

In a third aspect, the present invention is directed to a mouse-human chimeric anti-CD71 monoclonal antibody, or a functional fragment thereof, which comprises a variable region comprising at least one heavy chain of SEQ ID No. 1 and at least one light chain, the sequence of which is chosen between SEQ ID No. 2 and SEQ ID No. 11.

By "mouse-human chimeric antibody", it is meant herein an antibody wherein the variable region is murine-derived whereas the constant region is of human origin. A number of methods for producing such chimeric antibodies have yet been reported, thus forming part of the general knowledge of the skilled artisan.

According to another embodiment, the mouse-human chimeric anti-CD71 monoclonal antibody, or the functional fragment thereof, comprises a variable region comprising at least one heavy chain encoded by SEQ ID No. 3 and at least one light chain encoded by a sequence chosen between SEQ ID No. 4 and SEQ ID No. 12.

In yet another embodiment, the chimeric antibody, or the functional fragment thereof, further comprises a constant region comprising:
- at least one heavy chain of a sequence selected from SEQ ID No. 5 and SEQ ID No. 9; and/or
- at least one light chain of SEQ ID No. 6.

In yet another embodiment, the chimeric antibody, or the functional fragment thereof, further comprises a constant region comprising:
- at least one heavy chain encoded by a sequence selected from SEQ ID No. 7 and SEQ ID No. 10; and/or
- at least one light chain encoded by SEQ ID No. 8.

According to a fourth aspect, the present invention concerns a coupling product between an anti-CD71 monoclonal antibody as herein described, and a bioactive molecule.

Such a bioactive molecule may be selected from:
A) Metals:
Metals are selected from radio-isotopes and non-radioactive metals, such as gadolinium useful for NMR. Preferably, metals are radioactive isotopes such as:
gamma emitters (e.g., $I^{131}$);
beta emitters (e.g., $Y^{90}$, $Lu^{177}$);
alpha emitters (e.g., $Bi^{212}$, $Bi^{213}$, $Ac^{225}$ $At^{211}$).
The main radio-isotopes used for therapeutic or diagnostic purposes are: Actinium 225, Actinium 227, Arsenic 72 (PET imaging), Astatine 211, Bismuth 212 and 213, Bromine 75 (PET imaging), Bromine 77, Cobalt 55 (PET imaging), Copper 61 (PET imaging), Copper 64 (PET imaging and treatment), Copper 67 (PET imaging), Iodine 123 (PET imaging), Iodine 131, Lutetium 177 (PET imaging and treatment), Osmium 194, Radon 223, Rhenium 186, Ruthenium 105, Terbium 149, Thallium 228 and 229, Yttrium 90 and 91.
These isotopes may be directly linked to the antibody, or indirectly through a chelating agent such as macrocycles, DTA, DTPA.
In any case, coupling the antibody and the isotope, or coupling the antibody and the chelating agent/isotope may be either direct or indirect via a linker.
B) Toxins or Cell Poisons:
Various toxic molecules may be used such as diphtheria toxin (A chain), *Pseudomonas* exotoxin, ricin (A chain), abrin, pokeweed antiviral peptide (PAP), tricathecum, and functional fragments thereof. Here also, the coupling may be either direct or via a linker.
C) Drugs:
Suitable drugs are cytotoxic and/or cytolytic. Examples are interferon, methotrexate, doxorubicin, daunorubicin, vinblastin, mitomycin C, bleomycin, taxol, taxotere, navelbine, adriamycin, and the like.
Drugs may be used either directly or via a linker.
D) Galenic Vectors:
This may be interesting for improving antibody transport, half-life, cell penetration, therapeutic efficiency ...
Various vectors may be used (liposomes, nanoparticles, polymers, cationic emulsions, anionic emulsions, neutral emulsions, dendritomas, and the like).
Advantageously, the galenic vector may carry another bioactive molecule such as a radioisotope, a drug, a toxin, a nucleic acid, especially an antisense RNA.
Again, the coupling may be direct or indirect, via a linker.
E) Biological Molecules Capable of Binding to a Given Cell Type:
Examples are antibodies, regardless or not of their recognition specificity, bispecific antibodies, recombinant proteins.
The purpose is here to obtain at least bispecific molecules.
F) Enzymes:
Examples are RNAses.
G) Nucleic Acids:
Antibodies may be coupled, directly or not, to nucleic acids or synthetic oligonucleotides, such as antisense RNAs.
H) Biotin-, Streptavidin-, or Avidin-Type Molecules:
Such molecules are interesting for improving the antibody binding specificity.
More particularly, a coupling product according to the present invention will incorporate a bioactive molecule selected from:
beta-, alpha- or gamma-emitting radioisotopes;
toxins or functional fragments thereof, such as toxic A chain ricin or abrin type molecules and A chain diphtheria toxin;
cytolytic drugs such as methotrexate, mitomycin, adriamycin;
galenic vectors such as liposomal vectors and cationic emulsions, advantageously including antisense RNA;
biological molecules capable of binding to a given cell type such as antibodies or recombinant proteins, for obtaining bispecific molecules;
RNAses;
antisense RNAs;
biotin, avidin or streptavidin.
In some embodiments, the coupling product comprises a linker, preferably a C5 to C15 linker, so that the bioactive molecule is released when the coupling product is contacted with, e.g., esterase prodrug.
According to a fifth aspect, the present invention is related to a pharmaceutical composition comprising:
at least one anti-CD71 monoclonal antibody as described herein, or at least one functional fragment thereof; or
at least one coupling product as defined above,
and a pharmaceutically acceptable carrier.
In a preferred embodiment, the pharmaceutical composition of the invention further comprises human leukocyte effector cells that express or have the potential to express Fc receptors for antibody and that are capable of mediating antibody dependent cellular cytotoxicity (ADCC) reaction against target cells.
In this respect, said human leukocyte effector cells may advantageously be selected from lymphocytes, monocytes, macrophages, NK cells, granulocytes, eosinophils, and mast cells.
A sixth aspect of the present invention concerns a method for inhibiting proliferation and/or killing malignant tumour cells, comprising providing to a patient in need thereof at least one substance selected from:
anti-CD71 monoclonal antibodies as described above, or functional fragments thereof or constructions including such fragments;
coupling products as mentioned above; and
pharmaceutical compositions as defined above;
under conditions and in an amount sufficient for the binding of said substance to the malignant tumour cells, thereby causing inhibition of proliferation of and/or killing of the malignant tumour cells.
The term "construction including a fragment of an antibody" means a product of a polynucleotide sequence coding for said fragment and a polypeptide with a stabilizing or transport function, such as albumin, ovalbumin or a fragment thereof. It can also mean a conjugate combining the antibody or antibody fragment with an adjuvant and/or a molecule or structure ensuring transport and/or stability of said antibody, such as liposomes, cationic vesicles or emulsions, or nanoparticles. Yet, it can mean a combination of the product of a sequence as described above conjugated with an adjuvant and/or a molecule or structure ensuring transport and/or stabilization of the molecule.
The therapeutic methods encompassed by the present invention involve primary tumors or cancers, but are advantageously useful for treating metastases. As an example, a method for inhibiting or killing malignant tumour cells comprises administering to a patient one or more of the substance described above, under conditions sufficient for the binding of the monoclonal antibody, or binding fragment, to malignant tumour cells in the patient. The binding of antibodies, or their binding fragments, to the tumour cells induces the inhibiting or killing of the cells by the patient's immune cells.
Such antibody-mediated treatment or therapy may also be accompanied by other treatments that are directed to tumour or cancer cells, for example, radiation, chemotherapy, and the like, as well as by adjunctive therapies to enhance the immune system's attack on the opsonized cancer or tumour cells following the above-described treatment/therapy procedure(s).

More particularly, when using a pharmaceutical composition as defined above as further comprising human leukocyte effector cells, said human leukocyte effector cells are autologous or allogeneic cells of said patient in need of inhibiting the proliferation of and/or killing malignant tumour cells. Practically, cells will be obtained from the patient or from a donor by cytapheresis and, in some cases, elutriation. They will be injected back fresh either after treatment with the substance, or after short term culture in the presence of cytokines (as IL2) or growth factor (GM-CSF and IL4), or after freezing (as in autotransfusion)

In an embodiment, said malignant tumour cells are selected from cells of solid tumours. These cells are for instance cells of metastatic cutaneous melanoma, metastatic uveal melanoma, glioblastoma, renal cell carcinoma, hepatocarcinoma (HCC), ovarian adenocarcinoma, pancreas adenocarcinoma, non small cell lung carcinoma (NSCLC), breast adenocarcinoma, colorectal adenocarcinoma, hematological malignancies. Preferably, malignant tumour cells are cells of metastatic cutaneous melanoma or of metastatic uveal melanoma.

Advantageously, the aforementioned method further comprises, prior to said providing, a step of depleting intracellular transferrin level and/or intracellular iron level in said malignant tumour cells. For instance, intracellular iron level may be depleted using deferoxamine or ferritin.

Moreover, in the method of the invention, the substance as described above is further capable of enhancing the immune response in said patient by binding to regulatory T cells. Indeed, since CD71 is expressed by regulatory T cells, it is thus possible to block inhibition of the immune response by regulatory T cells upon binding of anti-CD71 monoclonal antibodies thereto.

Besides, the substance as referred to above may be used 1) to diagnose fetopathy by identifying fetal nucleated red blood cells and to sort the fetal red blood cells; 2) to determine the type of anemia in an anemic patient by looking at the transferrin receptor/ferritin ratio; 3) to identify micrometastases with proliferating cells and to sort them.

In addition, the substance may be used ex vivo to purge proliferating cells from peripheral blood CD34+ stem cells obtained after injection of GM-CSF for autologous graft. It may also be used to deplete activated cells from cord blood or from bone marrow. Yet it may be used instead of anti CD25 mAb to deplete activated/proliferating cells, since resting T reg cells do not express CD71 while they express CD25.

The foregoing substance may also be used in vivo 1) to treat ATL and HTLV1+ T cell leukemia; 2) to deliver a drug or another antibody (possibly combined in a bispecific mAb or in an avidin fusion protein) across the blood-brain barrier.

According to a seventh aspect, the present invention is directed to an isolated nucleic acid molecule, comprising one or more of the nucleotide sequences depicted in SEQ ID Nos. 3, 4, and 12. Said sequences encode the heavy and light chains of the variable region of a mouse anti-CD71 antibody, respectively.

An eighth aspect of the invention relates to an expression vector comprising a nucleic acid molecule as described above.

A ninth aspect concerns an host cell or an host organism comprising an expression vector of the invention.

In a tenth aspect, the present invention is related to a method for producing a chimeric antibody as described above, comprising:

a) transforming a suitable host cell with at least one expression vector of the invention;
b) culturing said host cell under conditions favoring expression; and
c) purifying assembled chimeric antibodies from the culture medium.

According to another embodiment, the method for producing a chimeric antibody of the invention comprises:
a) transforming a suitable host cell with at least one expression vector which comprises: (i) a nucleic acid molecule as described above; and (ii) one or more of the nucleotide sequences depicted in SEQ ID Nos. 7, 8, and 10, these sequences encoding heavy or light chains of the constant region of human gamma immunoglobulins;
b) culturing said host cell under conditions favouring expression; and
c) purifying assembled chimeric antibodies from the culture medium.

An eleventh aspect of the present invention relates to an isolated polynucleotide encoding an anti-CD71 monoclonal antibody as disclosed herein.

According to a twelfth aspect, the present invention concerns an ex vivo method for depleting CD71-positive cells in a patient in need thereof, comprising:
a) contacting a biological sample from said patient with at least one substance selected from:
    anti-CD71 monoclonal antibodies of the invention, or functional fragments thereof or constructions including such fragments;
    coupling products as disclosed herein; and
    pharmaceutical compositions as described above;
wherein said biological sample is likely to contain CD71-positive cells;
b) eliminating the complexes formed between said substance and the CD71-positive cells contained in said biological sample; and
c) recovering a "purged" biological sample.

Preferably, the method of the invention further comprises a step of returning said "purged" biological sample to said patient.

In one embodiment, said biological sample is selected from a bone marrow sample, blood enriched in CD34+ cells, cord blood pluripotent stem cells, stem cells.

In another embodiment, said patient has been transplanted or is in need of transplantation, e.g., with autologous or allogenic bone marrow. Alternatively, said patient has a cancer and, for instance, he/she needs autologous CD34+ stem cell transplant depleted in malignant proliferating cells after receiving high doses radio- or chimiotherapy. Yet alternatively, said patient may have a disorder selected from auto-immune and neuro-immune disorders.

According to a thirteenth aspect, the present invention relates to a method for enhancing the immune response in a patient having a cancer, comprising providing to said patient at least one-substance selected from:
    anti-CD71 monoclonal antibodies as defined above or functional fragments thereof or constructions including such fragments;
    coupling products as described above; and
    pharmaceutical compositions as herein disclosed;
under conditions and in an amount sufficient for the binding of said substance to regulatory T cells, thereby blocking inhibition of said immune response by said regulatory T cells.

In particular, such a substance, and especially anti-CD71 monoclonal antibodies, are useful as immunotherapy/vaccine adjuvants.

In an embodiment, the patient has a melanoma, especially a cutaneous or an uveal melanoma, or an ovarian cancer or a liver cancer.

Other embodiments and advantages of the present invention are illustrated in the following non-limiting examples.

EXAMPLES

I-1—Materials and Methods
I-1—Production and Purification of mAb

MAbs were obtained by immunizing BALB/c mice or Biozzi high responder mice with human Thymic T cell clones (BA120g—also called BA120 and deposited at the CNCM on Jun. 14, 2005, under number CNCM I-3449-, CY1G4, BB27) or thymic cells (O275) as previously described (Boumsell L. et al, 1980). Cell fusions were carried out with NS1 as described (Gouttefangeas C. et al., 1992).

Screening was performed in two stages. Following indirect immunofluorescence staining and flow cytometry analysis all hybridoma supernatants reacting with the immunizing cells were retained. Further on, the supernatant reacting with a high intensity with activated cells and not with resting cells were kept. The culture containing the selected mAb was cloned twice by limiting dilutions. Ascites fluid was obtained from Balb/c mice or nude mice primed with pristane or incomplete freund adjuvant. The ascites was dialyzed against phosphate-buffered saline (PBS), purified on protein G column and sterilized by ultrafiltration and further utilized at the indicated concentration. BA120g, O275 and BB27 were of IgG1, CY1G4 of IgG2a and IVG42 of IgG2b isotype as determined with an ELISA isotyping kit. O275 was shown by immunoprecipitaiion and tissue distribution to recognize CD2, while BB27 recognizes CD101. These antibodies were selected as negative control as they are of the IgG1 isotypes, the CD2 and CD101 molecules are lacking on melanocytes cell lines, CD2 is expressed by NK cells and not monocytes, while CD101 is expressed by monocytes only.

I-2—Cells and Cell Lines

Human PMNC were prepared by Ficoll-Hipaque (F/H) density gradient centrifugation. Mononuclear cells were obtained after informed consent from healthy volunteers. Monocytes, NK cells or T cells were isolated using the appropriate stemcell rosette sep depletion system, as described by the manufacturer (Stem cell technologies, Grenoble, France).

Cultures of human melanoma cell lines A375, M74 and Dauv1 and other cell lines were maintained in logarithmic growth in RPMI 1640 containing 10% FCS and antibiotics at 37° C. in a 5% $CO_2$ incubator. A375, M74 and Dauv1 were selected because they were previously shown to represent various level of sensitivity to apoptosis. Briefly, Dauv 1 and M74 are sensible to Fas only in the presence of IFN γ and resistant to TNF, anti-Fas, and Trail. In contrast, A 375 is sensible to all aforementionned signals except IFN γ alone.

Adherent cell lines were harvested by standard trypsinization (0.5 mg/ml trypsin in 0.02 mM glucose/PBS). All cell cultures were checked for mycoplasma contamination.

Other Cell lines in culture used were Dev (medulloblastoma), Jurkat (T cell leukemic line), C8166 (HTLV1+ cell line), and K562 (erythroleukemia).

I-3—Immunofluorescent Staining and Flow Cytometry

Indirect immunofluorescence was performed with purified mAbs using FITC-conjugated antimouse IgG provided in the Qifiquit (DakoCytomation, Trappes, France). Quantitative Flow cytometry analysis was performed with a single laser XL analyzer Epics (Coulter, Miami, Fla.) as previously described I-4—Proliferation Assays Cells were cultured for 4 days in the presence or absence of various concentrations of purified mAb in 96 well flat bottom tissue culture plates. Usually 5 μg purified mAb (25 μg/ml) were added per 0.2 ml well at the initiation of the culture. Cells were pulsed with 1 mCi of $^3$H[TdR] during the last 12-16 h of culture. $^3$H[TdR] incorporation was measured using a liquid scintillation counter (Topcount, Packard instrument, Meridien, Conn.).

I-5—Cross-Bloking Experiments and Biotynilated OKT9 Binding Analysis

A375 cells were incubated for 30 minutes with BA120g, CY1G4, Tf-Fe or NS1 ascites fluid at 4° C. or 37° C. before biotin-labeled anti-CD71 mAb OKT9 was added and incubated for another 20 min. Next, after one wash, streptavidin-fluorescein was added and cells were analysed by flow cytometry. Mean fluorescence intensity was recorded as set forth in Table 2 hereafter.

Ba120G et Cy1G4: 15 μg (saturating conditions)
Control Ascites NS1: 2 μl
OKT9-Blot: 1 μl II—Results II-1—Kinetics of the Anti-CD71 BA120g Induced Inhibition of A375 Melanoma Cell Line Proliferation Previous reports have shown that only very few anti-CD71 mAb can inhibit cell proliferation. It was hypothetized that extensive receptor cross-linking was required for significant inhibition of tumour cell growth (Taetle et al., 1986, Lesley et al., 1985). This could explain why IgG anti-CD71 mAb, although inducing down-modulation and degradation of the transferrin receptor were ineffective in inhibiting cell growth.

Figure 1:
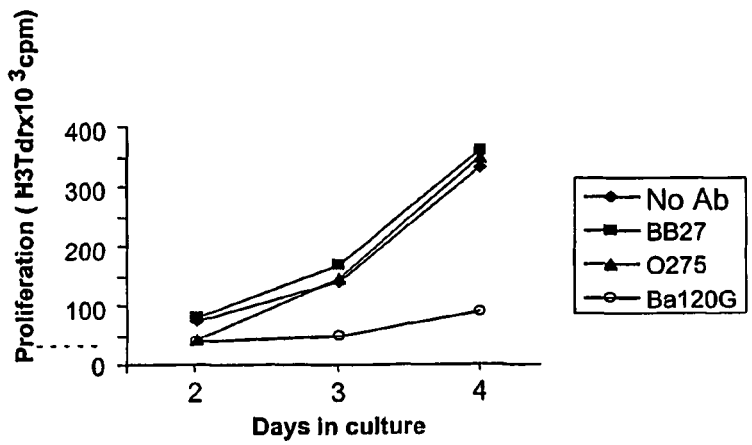
FIG. 1. Kinetic of the inhibition of the melanoma cell line A375 proliferation induced by anti-CD71 mAb BA120g.

Using $10^3$ (or $5 \times 10^3$) A375 cells per well, $^3$H[Tdr] incorporation was maximal at day 4 (FIG. 1), and sharply decreased thereafter (not shown). There was no modification of the kinetic of the proliferation in the presence of 5 μg (25 μg/ml) of anti-CD2"O275" or anti-CD101"BB27" mAb, both of the IgG1 isotype. In contrast, in the presence of anti-CD71 mAb BA120g of the IgG1 isotype, a plateau was observed from day 2 to day 4 (FIG. 1).

II-2—Anti-CD71 BA120g Inhibits all Cell Lines Proliferation

It was a goal to determine whether the BA120g-induced inhibition of cell proliferation was observed with other cell lines. Therefore, in addition to A375, the melanoma cell lines M74 and Dauv1, the T cell lines Jurkat and HTLV1+ cell line C8166, the erythroleukemic cell line K562, and the medulloblastoma cell line Dev were tested. In all cases, BA120g induced a high level of inhibition at day 4, as shown on FIG. 2, reaching over 70% inhibition in every case.

II-3—Only the Anti-CD71 mAb BA120g Inhibits A375 Melanoma Cell Line Proliferation An inhibitory effect of the two other anti-CD71 mAbs on A375 proliferation was looked for. CY1G4 is of the IgG2a isotype, while 4G42 is an IgG2b. The three mAbs had previously been shown to be anti-CD71 mAbs by tissue distribution and by immunoprecipitation. As can be seen on FIG. 3, only BA120g inhibited A375 cell proliferation, while CY1G4 (shown on FIG. 3) and 4G42 (not shown) did not modify A375 proliferation.

II-4—Quantification of Anti CD71 Binding Sites on Melanoma Cell Lines

It was a goal to study whether the differences of the anti-CD71 mAbs in their ability to inhibit cell growth was related to differences in their respective binding to melanoma cells. Comparative analysis of the number of sites identified by BA120g and CY1G4 on the three melanoma cell lines A375, Dauv1 and M74, and on the medulloblastoma cell line DEV was performed. Therefore, standardized FITC coupled anti mouse immunoglobulin antibody and calibration beads (Qifikit) was used. Table 1 shows that the number of anti-CD71 binding sites was similar for the 2 mAbs and even slightly higher for CY1G4. In addition, Table 1 shows that the number of binding sites was higher for the 3 melanoma cell lines than for Dev, the medulloblastoma cell line whose proliferation was however inhibited by BA120g (shown in FIG. 2).

TABLE 1

| Cell line | Sites/cell (×10⁻³) | |
|---|---|---|
| | Cy1G4 | Ba120G |
| A375 | 6.5 | 3.9 |
| M74 | 8.5 | 6.9 |
| Dauv1 | 7.1 | 6.1 |
| Dev | 3.2 | 2.2 |

II-5 Studies of BA120g Binding Sites

Whether BA120g was binding to the same epitope as a reference anti-CD71 antibody OKT9, known to bind to a different site on the transferrin receptor than its ligand ferritransferrin, was investigated. To do so, cross-blocking experiments were performed, in which the first incubation of the melanoma cells took place with either a control ascites, NS1, or the 2 anti-CD71 mAb, BA120g or CY1G4, or ferritransferrin. Next directly biotynilated OKT9 binding was analysed as described. The results shown in Table 2 below clearly indicated that, while CY1G4 was able to inhibit OKT9 binding, both BA120g and ferritransferrin were binding a different epitope on CD71. In other words, BA120g identifies a different epitope from both CY1G4 or OKT9 or from its ligand ferritransferrin.

TABLE 2

| Experimental conditions | Mean Fluorescence intensity |
|---|---|
| NS1 + OKT9-Biot; 4° C. | 6.53 |
| Ba120G + OKT9-Biot; 4° C. | 6.03 |
| Cy1G4 + OKT9-Biot; 4° C. | 2.44 |
| Tf-Fe + OKT9-Biot; 4° C. | 5.27 |
| NS1 + OKT9-Biot; 37° C. | 8.84 |
| Ba120G + OKT9-Biot; 37° C. | 11.4 |
| Cy1G4 + OKT9-Biot; 37° C. | 2.51 |
| Tf-Fe + OKT9-Biot; 37° C. | 15.3 |

II-6 BA120g Binding is not Blocked by the Ligand of CD71, Ferritransferrin, nor by Human AB Serum Human serum contains both ferritransferrin and soluble transferrin receptors. Therefore, it was important to determine whether either ferritransferrin or human serum blocked the binding of BA120g to cells. As shown in Table 3 below, in the presence of 10% human AB sera, the binding of BA120g was increased, when compared to the binding in the presence of 10% fetal calf serum. Further, the addition of ferritransferrin, even to human AB sera, only slightly decreased the binding of BA120g. So, the number of BA120g binding sites on A375 melanoma cell line is not significantly modified in the presence of human AB sera or ferritransferrin.

TABLE 3

| Mab | Medium | Tf-Fe | Sites | Anti-CD71 Specific* |
|---|---|---|---|---|
| NS1 | FCS | no | 3246 | |
| BA120g | FCS | no | 21741 | 18495 |
| NS1 | AB | no | 5794 | |
| BA120g | AB | no | 33976 | 28182 |
| NS1 | FCS | yes | 3313 | |
| BA120g | FCS | yes | 18040 | 14727 |
| NS1 | AB | yes | 5794 | |
| BA120g | AB | yes | 30618 | 24824 |

REFERENCES

Collawn J F. et al., (1993) J. Biol. Chem. 268: 21686-92
Haddad E. et al., (2003) J. Am. Soc. Nephrol. 14: 327-37
Lee H J. et al., (2000) J. Pharmacol Exp. Ther. 292:1048-52
Li H. et al., (2002) Trends in Pharmalogical Sciences 23: 206-209
Ng P P. et al., (2002) Proc. Natl. Acad. Sci. USA 6:99:10701-11
Shinohara et al., (2000) Int. J. Oncol. 17: 643-51
Zech N H. et al., (2003) J. Hematother Stem Cell Res. 12: 367-73
Bismuth G. et al., (2002) Sci STKE. 2002 Apr. 16; 2002 (128): RE4. Review
Ugurel S. et al., (2004) Cancer Immunol. Immunother. Jan. 16
Noronha E J. et al., (1998) J. Immunol. 161:2968-2976
Mills L. et al., (2002) Cancer Res. 62: 5106-14
Soiffer R J. et al., (1997) Clin. Cancer Res. 3: 17-24
Lee et al., (2001) Cancer Res. 61: 4474-82
Harris M. (2004) The Lancet Oncology vol 5: 292
Cancer Highlights (BioSeeker Group) No. 2 (2004)
Levy J. E., et al. (1999) Nature genetics, 21: 396-399,
Larrick J. W. and Hyman E. S., (1984) N. Engl. J. Med. 311: 214-218
Boumsell L, Bernard A. (1980) J. Immunol. Methods. 38:225-9
Gouttefangeas C, et al., (1992) Eur J. Immunol. 22:2681-5
Taetle et al., (1986) Cancer Res. 46 (4 Pt1): 1759-63
Lesley et al., (1985) Mol. Cell. Biol. 5(8): 1814-21

The invention claimed is:

1. A method for inhibiting proliferation or killing CD71 positive malignant tumor cells, comprising providing to a patient in need thereof
   an anti-CD71 monoclonal antibody or an antigen-binding fragment thereof, wherein said anti-CD71 monoclonal antibody comprises
   (a) at least one heavy chain variable region comprising the amino acid sequence of SEQ ID No. 1 and at least one light chain variable region comprising an amino acid sequence selected from the group consisting of SEQ ID No. 2 and SEQ ID No. 11; or
   (b) at least one heavy chain variable region encoded by a nucleic acid molecule comprising the nucleotide sequence of SEQ ID No. 3 and at least one light chain variable region encoded by a nucleic acid molecule comprising a nucleotide sequence selected from the group consisting of SEQ ID No. 4 and SEQ ID No. 12
   under conditions and in an amount sufficient for the binding of said anti-CD71 monoclonal antibody to the malignant tumor cells, thereby causing inhibition of proliferation or killing of the malignant tumor cells.

2. The method according to claim 1, wherein said malignant tumor cells are selected from cells of metastatic cutaneous melanoma, metastatic uveal melanoma, glioblastoma, renal cell carcinoma, hepatocarcinoma (HCC), ovarian adenocarcinoma, pancreas adenocarcinoma, non small cell lung carcinoma (NSCLC), breast adenocarcinoma, colorectal adenocarcinoma, and hematological malignancies.

3. The method according to claim 1, further comprising, prior to said providing, a step of depleting intracellular transferring level and/or intracellular iron level in said malignant tumor cells.

4. A method for producing a chimeric antibody that binds CD71, comprising:
   a) transforming a suitable host cell with at least one expression vector comprising two or more of the nucleotide sequences depicted in SEQ ID Nos. 3, 4, and 12;
   b) culturing said host cell under conditions favoring expression; and
   c) purifying assembled chimeric antibodies from the culture medium.

5. A method for producing a chimeric antibody that binds CD71, comprising:
   a) transforming a suitable host cell with at least one expression vector which comprises: (i) a nucleic acid molecule comprising two or more of the nucleotide sequences depicted in SEQ ID Nos. 3, 4, and 12; and (ii) one or more of the nucleotide sequences depicted in SEQ ID Nos. 7, 8, and 10;
   b) culturing said host cell under conditions favoring expression; and
   c) purifying assembled chimeric antibodies from the culture medium.

* * * * *